Aug. 6, 1963 G. KUBO Plant Pat. 2,271
VERBENA PERUVIANA PLANT
Filed May 3, 1962
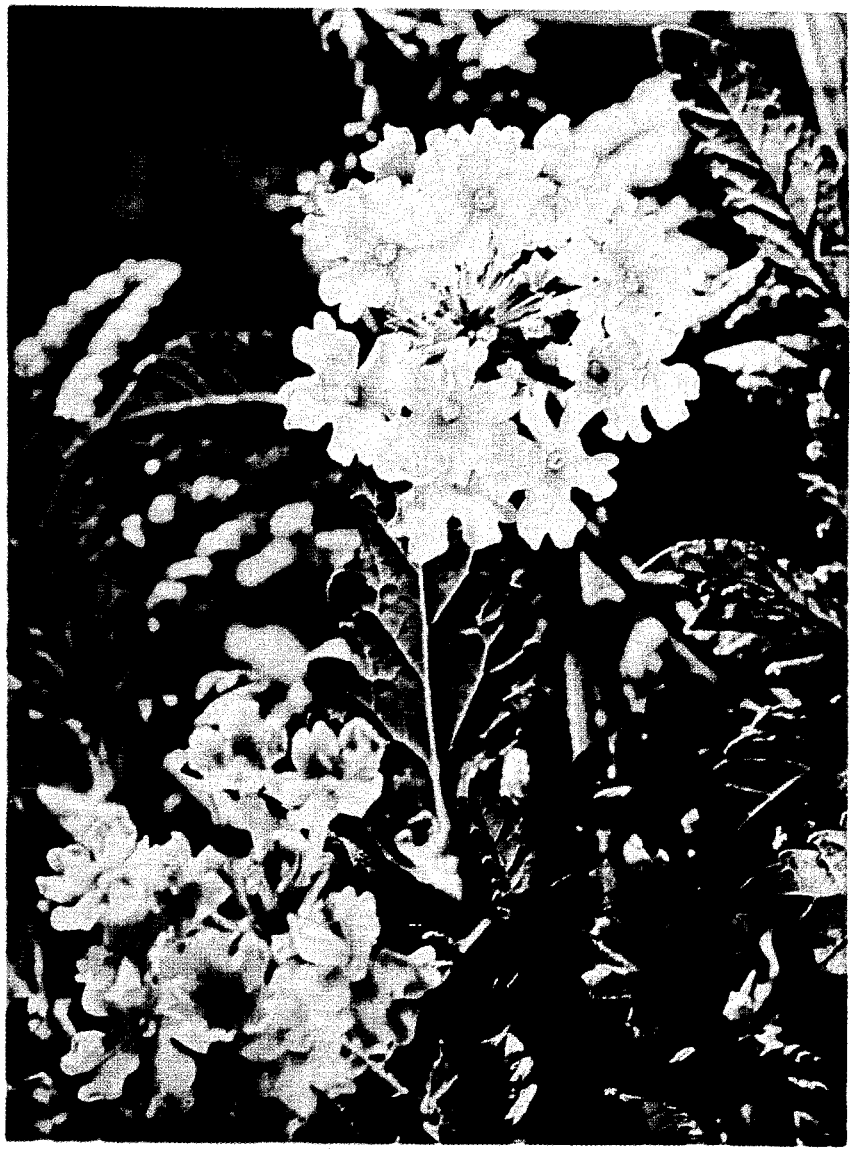
INVENTOR.
GEORGE KUBO
BY J. F. Cuneo
ATTORNEY United States Patent Office Plant Pat. 2,271
Patented Aug. 6, 1963

2,271
*VERBENA PERUVIANA* PLANT

George Kubo, Anaheim, Calif., assignor to Samuel R. Fujimoto and Raymond S. Fujimoto, both of Gardena, Calif.

Filed May 3, 1962, Ser. No. 192,298
1 Claim. (Cl. Plt.—87)

This invention provides a new and distinct variety of *Verbena peruviana* plant of the prostrate type.

The new and distinct variety is characterized by its unique variegated blooms that have a light pink to white outside coloring, inner bright red areas surrounding the center that vary in size from flower to flower, with many of the flowers having a zone of varying area between the dark central portion and the light-colored outer edge of the corolla, that is lighter red than the central portion; by its rather large clusters of flowers that are born on long stiff upright stems; and by its rather thick leaves that are a medium bright green. The plant is of the ground cover type and its branches and leaves are best described as prostrate and spreading. This new variety exhibits a vigorous and hardy growth.

The new and distinct variety of *Verbena peruviana* was discovered by me as a sport growing in a cultivated bed of an ordinary unpatented variety of *Verbena peruviana* that is situated on my residential property located at 2888 West Lynrose Drive in the city of Anaheim, county of Orange, State of California. The sport was discovered in June of 1961.

The new variety has been reproduced asexually at 2888 West Lynrose Drive, Anaheim, California from cuttings and all of the descendants of this plant have exhibited the distinguishing characteristics of the new and distinct variety, thereby establishing that the strain is true. A large number of cuttings have been made since the new variety was discovered. The new species cannot be reproduced true from seed.

The accomnanying illustration in full color, shows typical specimens of the flower and leaves. The colors in the illustration are as correct as it is possible to reproduce them by this type of illustration.

A detailed description of the new variety of *Verbena peruviana* follows. To facilitate identification of the important colors mentioned in this specification, the designations adopted by the British Horticultural Colour Charts have been followed.

*Flowers*

Locality where grown and observed: Anaheim, California.

Flowers borne: Clusters of individual flowers are borne on a stiff erect stem, the length of the stem varying between four and eight inches.

*Number of individual flowers.*—Generally from 12 to 14 individual flows are borne by one stem.

*Size of clusters.*—The flowers are arranged in the form of a rough circle that is from one and one-half inches to one and three-quarter inches in diameter.

Individual flowers:

*Size.*—Each individual flower is approximately one-half to nine-sixteenth inch in diameter.

*Color.*—The outer edge of each individual flower is Rose Pink 427/3, however, in warm weather this delicate color fades and often approaches white, particularly when the plant is growing outdoor. The central portion of the flower is, in the majority of flowers Turkey Red 421. The area having this color varies widely from flower to flower. That portion of the flower between the pink outer edge of the corolla and the central bright red portion is, in many of the flowers, Camellia Rose 622. Again the area having this color varies widely from flower to flower. The center of each individual flower has a pale yellow eye that is best identified as to color as Dresden Yellow 64/3.

*The Plant*

Habit: The plant is a prostrate type. The plant exhibits a vigorous growth and makes an excellent ground cover.

Blooming habit: The plant blooms abundantly from March to November in the area in which it was observed in sourthern California.

Leaves:

*Shape.*—The leaves are predominantly ovate in outline and have a cuneate base decurrent into the petiole; divisions are pinnatified into narrow, linear acute lobes. The leaves are strygose on the edges and especially on the veins.

*Texture.*—Thick leaves with prominent veins.

*Borne on stem.*—Leaves are generally opposite.

*Size.*—Mature leaves vary from one and one-half to one and three-quarter inches in length, and are approximately one-half inch in width at the widest portion.

*Color.*—Upper side—Parsley Green oo962/1. Under side—Parsley Green oo962/3. The leaves maintain their bright green color when exposed to the sun. In the winter, cold weather will tend to give the leaves a slight reddish cast, however, even in cold weather the leaves will remain brighter green than other species of *Verbena peruviana.*

Branches: The branches remain close to the ground and extend in all directions from the central portion of the plant.

Rooting: The plant is self rooting.

Aroma: The blooms of the plant have no appreciable aroma but there is a slight aroma associated with the foliage.

I claim:

A new and distinct variety of Verbena plant substantially as illustrated and described, characterized by its variegated individual flowers with the outer edge of the corolla approximately Rose Pink, with bright red areas surrounding the center that vary in size from flower to flower, and with a lighter red zone in many of the flowers between the bright red area surrounding the center and the pink-edged corolla, said lighter red zone varying in size from flower to flower, by its clusters of many flowers borne on stiff erect stems, by its thick bright green leaves that are opposite each other on the stems, and by its vigorous growth.

No references cited.